(12) United States Patent
Keeler

(10) Patent No.: US 9,907,615 B2
(45) Date of Patent: *Mar. 6, 2018

(54) ECCENTRIC BALLOON LASER CATHETER

(71) Applicant: The Spectranetics Corporation, Colorado Springs, CO (US)

(72) Inventor: Jacob Keeler, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/595,237

(22) Filed: May 15, 2017

(65) Prior Publication Data

US 2017/0245934 A1    Aug. 31, 2017

Related U.S. Application Data

(60) Continuation of application No. 14/175,359, filed on Feb. 7, 2014, now Pat. No. 9,649,159, which is a
(Continued)

(51) Int. Cl.
*A61B 18/18* (2006.01)
*A61B 18/24* (2006.01)
(Continued)

(52) U.S. Cl.
CPC ............ *A61B 18/24* (2013.01); *A61B 18/20* (2013.01); *A61M 25/104* (2013.01); *A61M 25/1002* (2013.01)

(58) Field of Classification Search
CPC .................. A61B 18/24; A61B 18/245; A61B 2017/22051; A61B 2017/22052; A61B 2017/22061
See application file for complete search history.

(56) References Cited

U.S. PATENT DOCUMENTS 4,053,845 A    10/1977   Gould
4,445,892 A    5/1984    Hussein et al.
(Continued)

FOREIGN PATENT DOCUMENTS

EP    165301 B1    4/1991
EP    2015672 B1   1/2009
(Continued)

OTHER PUBLICATIONS

Extended Search Report for European Patent Application No. 09833795.9 dated Apr. 12, 2012, 6 pages.
(Continued)

*Primary Examiner* — John R Downey
(74) *Attorney, Agent, or Firm* — Faegre Baker Daniels LLP

(57) ABSTRACT

Various embodiments of an eccentric balloon catheter are disclosed. In some embodiments, an eccentric balloon catheter includes an eccentrically positioned guidewire tube, with an interior lumen, that extends at least a portion of the length of the catheter body. Optical fibers may extend the length of the catheter body and may also be eccentrically positioned within the catheter body. An inflatable balloon may be positioned within a window within the catheter body near the distal end of the catheter. When inflated, the balloon and catheter may slide relative to one another. When used within a vessel, an inflated balloon may press against a vessel wall and bias the catheter toward an opposite vessel wall.

20 Claims, 12 Drawing Sheets

Related U.S. Application Data division of application No. 12/337,190, filed on Dec. 17, 2008, now Pat. No. 8,702,773.

(51) Int. Cl.
*A61B 18/20* (2006.01)
*A61M 25/10* (2013.01)

(56) References Cited

U.S. PATENT DOCUMENTS

| | | |
|---|---|---|
| 4,641,912 A | 2/1987 | Goldenberg |
| 4,669,467 A | 6/1987 | Willett et al. |
| 4,686,979 A | 8/1987 | Gruen et al. |
| 4,732,448 A | 3/1988 | Goldenberg |
| 4,747,405 A | 5/1988 | Leckrone |
| 4,784,132 A | 11/1988 | Fox et al. |
| 4,799,754 A | 1/1989 | Goldenberg |
| 4,807,620 A | 2/1989 | Strul et al. |
| 4,830,460 A | 5/1989 | Goldenberg |
| 4,844,062 A | 7/1989 | Wells |
| 4,848,336 A | 7/1989 | Fox et al. |
| 4,886,496 A | 12/1989 | Conoscenti et al. |
| 4,924,863 A | 5/1990 | Sterzer |
| 5,016,964 A | 5/1991 | Donnelly |
| 5,040,548 A | 8/1991 | Yock |
| 5,041,108 A | 8/1991 | Fox et al. |
| 5,042,976 A * | 8/1991 | Ishitsu .................. A61M 25/10 |
| | | 604/915 |
| 5,188,632 A | 2/1993 | Goldenberg |
| 5,250,045 A | 10/1993 | Bohley |
| 5,250,069 A | 10/1993 | Nobuyoshi et al. |
| 5,263,952 A | 11/1993 | Grace et al. |
| 5,263,953 A | 11/1993 | Bagby |
| 5,300,085 A | 4/1994 | Yock |
| 5,304,171 A | 4/1994 | Gregory et al. |
| 5,350,375 A | 9/1994 | Deckelbaum et al. |
| 5,350,395 A | 9/1994 | Yock |
| 5,352,197 A | 10/1994 | Hammersmark et al. |
| 5,415,653 A | 5/1995 | Wardle et al. |
| 5,429,604 A | 7/1995 | Hammersmark et al. |
| 5,429,617 A | 7/1995 | Hammersmark et al. |
| 5,451,233 A | 9/1995 | Yock |
| 5,456,680 A | 10/1995 | Taylor et al. |
| 5,470,330 A | 11/1995 | Goldenberg et al. |
| 5,484,433 A | 1/1996 | Taylor et al. |
| 5,514,128 A | 5/1996 | Hillsman et al. |
| 5,571,151 A | 11/1996 | Gregory |
| 5,573,531 A | 11/1996 | Gregory |
| 5,623,940 A | 4/1997 | Daikuzono |
| 5,643,251 A | 7/1997 | Hillsman et al. |
| 5,649,923 A | 7/1997 | Gregory et al. |
| 5,658,311 A | 8/1997 | Baden |
| 5,693,043 A | 12/1997 | Kittrell et al. |
| 5,722,972 A * | 3/1998 | Power .................. A61B 18/245 |
| | | 606/16 |
| 5,725,521 A | 3/1998 | Mueller |
| 5,817,144 A | 10/1998 | Gregory |
| 5,824,026 A | 10/1998 | Diaz |
| 5,836,946 A | 11/1998 | Diaz et al. |
| RE36,104 E | 2/1999 | Solar |
| 5,976,124 A | 11/1999 | Reiser |
| 5,989,243 A | 11/1999 | Goldenberg |
| 5,997,571 A | 12/1999 | Farr et al. |
| 6,022,342 A | 2/2000 | Mukherjee |
| 6,027,460 A | 2/2000 | Shturman |
| 6,036,715 A | 3/2000 | Yock |
| 6,066,130 A | 5/2000 | Gregory et al. |
| 6,090,118 A | 7/2000 | McGuckin et al. |
| 6,117,128 A | 9/2000 | Gregory |
| 6,210,393 B1 * | 4/2001 | Brisken .................. A61N 7/022 |
| | | 128/898 |
| 6,290,668 B1 | 9/2001 | Gregory et al. |
| 6,290,710 B1 | 9/2001 | Cryer et al. |
| 6,451,036 B1 * | 9/2002 | Heitzmann .... A61B 17/320758 |
| | | 606/159 |
| 6,458,098 B1 | 10/2002 | Kanesaka |
| 6,554,794 B1 | 4/2003 | Mueller et al. |
| 6,575,993 B1 | 6/2003 | Yock |
| 6,602,264 B1 | 8/2003 | McGuckin et al. |
| 6,613,038 B2 | 9/2003 | Bonutti et al. |
| 6,743,208 B1 | 6/2004 | Coyle |
| 6,824,550 B1 | 11/2004 | Noriega et al. |
| 6,872,206 B2 | 3/2005 | Edwards et al. |
| 7,037,316 B2 | 5/2006 | McGuckin et al. |
| 7,090,683 B2 | 8/2006 | Brock et al. |
| 7,169,141 B2 | 1/2007 | Brock et al. |
| 7,214,230 B2 | 5/2007 | Brock et al. |
| 7,252,664 B2 | 8/2007 | Nasab et al. |
| 7,329,223 B1 * | 2/2008 | Ainsworth ........... A61B 5/0084 |
| | | 600/300 |
| 7,371,210 B2 | 5/2008 | Brock et al. |
| 7,507,246 B2 | 3/2009 | McGuckin et al. |
| 7,628,763 B2 | 12/2009 | Noriega et al. |
| 7,674,253 B2 | 3/2010 | Fisher et al. |
| 7,744,608 B2 | 6/2010 | Lee et al. |
| 7,758,569 B2 | 7/2010 | Brock |
| 7,789,875 B2 | 9/2010 | Brock et al. |
| 7,930,065 B2 | 4/2011 | Larkin et al. |
| 8,043,314 B2 | 10/2011 | Noriega et al. |
| 8,052,704 B2 | 11/2011 | Olson |
| RE43,328 E | 4/2012 | Foley et al. |
| 8,353,922 B2 | 1/2013 | Noriega et al. |
| 8,409,136 B2 | 4/2013 | Wallace et al. |
| 8,414,505 B1 | 4/2013 | Weitzner et al. |
| 8,469,979 B2 | 6/2013 | Olson |
| 8,496,680 B2 | 7/2013 | Noriega et al. |
| 8,641,705 B2 | 2/2014 | Leo et al. |
| 8,684,952 B2 | 4/2014 | Weitzner et al. |
| 8,747,332 B2 | 6/2014 | Noriega et al. |
| 8,821,483 B2 | 9/2014 | Boutoussov et al. |
| 8,920,402 B2 | 12/2014 | Nash et al. |
| RE45,484 E | 4/2015 | Foley et al. |
| 9,028,489 B2 | 5/2015 | Choi |
| 9,028,499 B2 | 5/2015 | Keyak et al. |
| 9,060,793 B2 | 6/2015 | Larkin et al. |
| 9,066,742 B2 | 6/2015 | Splinter |
| 9,084,623 B2 | 7/2015 | Gomez et al. |
| 9,084,624 B2 | 7/2015 | Larkin et al. |
| 9,095,681 B2 | 8/2015 | Wenderow et al. |
| 9,101,380 B2 | 8/2015 | Larkin et al. |
| 9,113,955 B2 | 8/2015 | Noriega et al. |
| 9,119,609 B2 | 9/2015 | O'Sullivan et al. |
| 9,125,562 B2 | 9/2015 | Spencer et al. |
| 9,125,679 B2 | 9/2015 | Larkin et al. |
| 9,168,356 B2 | 10/2015 | Wenderow et al. |
| 9,173,713 B2 | 11/2015 | Hart et al. |
| 9,237,920 B2 | 1/2016 | Leo et al. |
| 9,241,733 B2 | 1/2016 | Olson |
| 9,254,143 B2 | 2/2016 | Huynh et al. |
| 9,261,259 B2 | 2/2016 | Shiomi et al. |
| 9,289,173 B2 | 3/2016 | Splinter |
| 9,289,258 B2 | 3/2016 | Cohen |
| 9,351,726 B2 | 5/2016 | Leimbach et al. |
| 9,351,727 B2 | 5/2016 | Leimbach et al. |
| 9,351,789 B2 | 5/2016 | Novichenok et al. |
| D775,728 S | 1/2017 | Cavada et al. |
| 9,649,159 B2 | 5/2017 | Keeler |
| 2002/0151879 A1 * | 10/2002 | Loeb ...................... A61B 18/22 |
| | | 606/15 |
| 2002/0188313 A1 | 12/2002 | Johnson et al. |
| 2003/0055398 A1 | 3/2003 | Imran |
| 2004/0015159 A1 | 1/2004 | Slater et al. |
| 2004/0079429 A1 | 4/2004 | Miller et al. |
| 2006/0094930 A1 | 5/2006 | Sparks et al. |
| 2006/0167442 A1 * | 7/2006 | Hebert .................. A61B 18/24 |
| | | 606/14 |
| 2006/0206182 A1 | 9/2006 | Pyles |
| 2007/0270787 A1 | 11/2007 | Winston et al. |
| 2007/0299496 A1 * | 12/2007 | Podmore ................ A61N 7/022 |
| | | 623/1.11 |
| 2008/0009673 A1 | 1/2008 | Khachi |
| 2008/0154345 A1 | 6/2008 | Taylor |
| 2008/0249515 A1 | 10/2008 | Taylor |
| 2008/0306499 A1 | 12/2008 | Katoh et al. |

(56) References Cited

U.S. PATENT DOCUMENTS

| | | | |
|---|---|---|---|
| 2009/0105686 A1* | 4/2009 | Snow | A61F 2/958 604/509 |
| 2009/0254072 A1* | 10/2009 | Khatib | A61B 18/24 606/7 |
| 2010/0114081 A1 | 5/2010 | Keeler et al. | |
| 2010/0137892 A1 | 6/2010 | Krolik et al. | |
| 2011/0292378 A1 | 12/2011 | Brown | |
| 2011/0319885 A1 | 12/2011 | Skwarek et al. | |
| 2013/0096545 A1 | 4/2013 | Laudenslager et al. | |
| 2013/0289672 A1 | 10/2013 | Hakomori et al. | |
| 2014/0031800 A1 | 1/2014 | Ben Oren et al. | |
| 2014/0171943 A1 | 6/2014 | Weitzner et al. | |
| 2014/0276594 A1 | 9/2014 | Tanner et al. | |
| 2015/0073340 A1 | 3/2015 | Pacheco et al. | |
| 2015/0150587 A1 | 6/2015 | Smith et al. | |
| 2015/0272664 A9 | 10/2015 | Cohen | |
| 2015/0342681 A1 | 12/2015 | Lee | |
| 2015/0349480 A1 | 12/2015 | Hongo et al. | |
| 2015/0359594 A1 | 12/2015 | Ben-Oren et al. | |
| 2015/0359595 A1 | 12/2015 | Ben Oren et al. | |
| 2016/0000454 A1 | 1/2016 | Rottenberg et al. | |
| 2016/0120603 A1 | 5/2016 | Grace et al. | |
| 2016/0151606 A9 | 6/2016 | Weitzner et al. | |
| 2016/0183844 A1 | 6/2016 | Splinter | |
| 2016/0184020 A1 | 6/2016 | Kowalewski et al. | |
| 2016/0192936 A1 | 7/2016 | Leimbach et al. | |
| 2016/0220300 A1 | 8/2016 | Cohen | |

FOREIGN PATENT DOCUMENTS

| | | |
|---|---|---|
| EP | 2282803 B1 | 2/2011 |
| WO | 2014118738 A1 | 8/2014 |
| WO | 2014158688 A1 | 10/2014 |
| WO | 2014182946 A2 | 11/2014 |
| WO | 2015089377 A1 | 6/2015 |
| WO | 2015159296 A1 | 10/2015 |
| WO | 2016069754 A1 | 5/2016 |

OTHER PUBLICATIONS

International Preliminary Report on Patentability for International Patent Application No. PCT/US2009/065557, dated Jun. 30, 2011, 6 pages.
International Search Report and Written Opinion issued in PCT/US2015/057834, dated Jan. 26, 2016, 11 pages.
International Search Report and Written Opinion issued in PCT/US2009/065557 dated Jan. 26, 2010, 12 pages.
Official Action for European Patent Application No. 09833795.9 dated Nov. 20, 2012, 4 pages.

* cited by examiner

ECCENTRIC BALLOON LASER CATHETER

CROSS REFERENCE TO RELATED APPLICATION

The present application is a continuation of U.S. application Ser. No. 14/175,359, entitled "ECCENTRIC BALLOON LASER CATHETER," filed on Feb. 7, 2014, issued as U.S. Pat. No. 9,649,159 on May 16, 2017, which is a divisional of U.S. application Ser. No. 12/337,190, entitled "ECCENTRIC BALLOON LASER CATHETER," filed on Dec. 17, 2008, issued as U.S. Pat. No. 8,702,773 on Apr. 22, 2014, which are hereby incorporated by reference in their entireties for all that they teach and for all purposes.

BACKGROUND

The embodiments described herein are generally directed to improved apparatus and methods for the delivery of laser energy, including without limitation, to a laser delivery catheter.

Arteries are the primary blood vessels that are responsible for providing blood and oxygen to the heart muscle. Arterial disease occurs when arteries become narrowed or blocked by a buildup of plaque (as some examples, atherosclerotic plaque or other deposits). When the blockage is severe, the flow of blood and oxygen to the heart muscle is reduced, causing chest pain. Arterial blockage by clots formed in a human body may be relieved in a number of traditional ways. Drug therapy, including nitrates, beta-blockers, and peripheral vasodilatator drugs to dilate the arteries or thrombolytic drugs to dissolve the clot, can be effective. If drug treatment fails, angioplasty may be used to reform or remove the atherosclerotic plaque or other deposits in the artery.

Traditional balloon angioplasty is sometimes used to address the blockage by inserting a narrow, flexible tube having a balloon into an artery in the arm or leg. The blocked area in the artery can be stretched apart by passing the balloon to the desired treatment site and gently inflating it a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion thereby requiring emergency procedures), the procedure known as excimer laser angioplasty may be indicated.

Excimer laser angioplasty procedure is similar in some respects to conventional coronary balloon angioplasty. A narrow, flexible tube, the laser catheter, is inserted into an artery in the arm or leg. The laser catheter contains one or more optical fibers, which can transmit laser energy. The laser catheter is then advanced inside the artery to the targeted obstruction at the desired treatment site. After the laser catheter has been positioned, the laser is energized to "remove" the obstruction.

In many procedures, the lesion is often engaged similar to conventional balloon angioplasty by crossing the blockage with a guidewire. The laser catheter's thin, flexible optical fibers facilitate the desired positioning and alignment of the catheter. Using the excimer laser, the clinician performs a controlled blockage removal by sending bursts of ultraviolet light through the catheter and against the blockage, a process called "ablation." The catheter is then slowly advanced through the blockage reopening the artery. If there are multiple blockages, the catheter is advanced to the next blockage site and the above step is repeated. When the indicated blockages appear to be cleared, the catheter is withdrawn.

However, due to the configuration of the optical fibers in most prior art laser catheters, the clinician is able to ablate only material that is typically directly in front of the distal end of the catheter. Thus, the debulked tissue area is limited to an area approximately the size of the optical fiber area at the distal end of the catheter. Typically, follow-up angioplasty is recommended.

Thus, it would be desirable to provide an apparatus and methods that could bias the distal end of the laser catheter in a desired direction to enable the clinician to ablate an area larger than the area of the distal end of the catheter. Furthermore, because plaque may be eccentric in a blood vessel and require directional control to adequately ablate the target area, it would be advantageous to provide an apparatus that is sufficiently flexible to travel and rotate around the target area so that the clinician may control the area to be ablated.

BRIEF SUMMARY

A laser catheter is provided according to one embodiment that includes a catheter body, a light guide, an inner tube and a balloon. The catheter body may include a central axis, a distal end, a proximal end, and a cavity disposed proximate to the distal end. The inner tube may include an port at the distal end of the catheter body and the inner tube positioned eccentric relative to the longitudinal central axis of the catheter body. The light guide may be disposed within the catheter body and may extend from the proximal end to the distal end of the catheter body. The balloon may be disposed within the cavity and slidably coupled with the catheter body allowing the catheter body to move relative to the balloon, and allowing the balloon to move relative to the catheter body.

A laser catheter is provided according to another embodiment that includes a catheter body, a guidewire tube, a light guide tube, and at least one fiber optic. The catheter body may include central axis (for example, a longitudinal central axis), a distal end, a proximal end, and a window disposed on the periphery of the catheter body proximate to the distal end. The guidewire tube may include an inner lumen located eccentrically within the catheter body and an aperture at the distal end of the catheter body. The light guide tube may have an inner lumen located eccentrically within the catheter body. The light guide tube may also include an aperture at the distal end of the catheter body. The light guide tube may extend from the proximal end of catheter body to the distal end of the catheter body. The at least one fiber optic may be disposed within the inner lumen of the light guide tube and extend the length of the light guide tube. The inflatable balloon may be disposed within the window of the catheter body.

In some embodiments, the laser catheter may include a straightening stylet coupled with the catheter body proximate to the cavity. In some embodiments, the balloon surrounds the inner tube. In some embodiments, a balloon rail may be coupled with the balloon and the catheter body. The balloon rail may be configured to allow the balloon to slide relative to the catheter body. In some embodiments, the laser catheter may also include a balloon tube disposed within the catheter body, coupled with the balloon, and configured to provide air to the balloon. In some embodiments, the cavity may be disposed within the periphery of the catheter body. In some embodiments, the cavity may be disposed proximate the inner tube, such that the inner tube is at least partially exposed by the cavity. In some embodiments, the light guide may include at least one optical fiber. In some embodiments, the inner tube may extend from the proximal end toward the distal end of the catheter body.

Further areas of applicability of the present disclosure will become apparent from the detailed description provided hereinafter. It should be understood that the detailed description and specific examples, while indicating various embodiments, are intended for purposes of illustration only and do not limit the scope of the disclosure.

BRIEF DESCRIPTION OF THE DRAWINGS

FIG. 3A is a representative longitudinal view with the balloon inflated, while FIG. 3B is a representative longitudinal view with the balloon deflated.

FIG. 4A is a representative perspective view with the balloon in a position near the distal end of the cavity, while FIG. 4B is a representative perspective view with the balloon in a position near the middle of the cavity.

FIG. 5A is a representative cross-sectional view of the balloon deflated, while FIG. 5B is a representative cross-sectional view of the balloon inflated.

FIG. 9A is a representative longitudinal view with the balloon deflated and positioned near the target, FIG. 9B is a representative longitudinal view with the balloon inflated and positioned near the target, and FIG. 9C is a representative longitudinal view with the balloon inflated and rotated about 180°.

Figure 1:
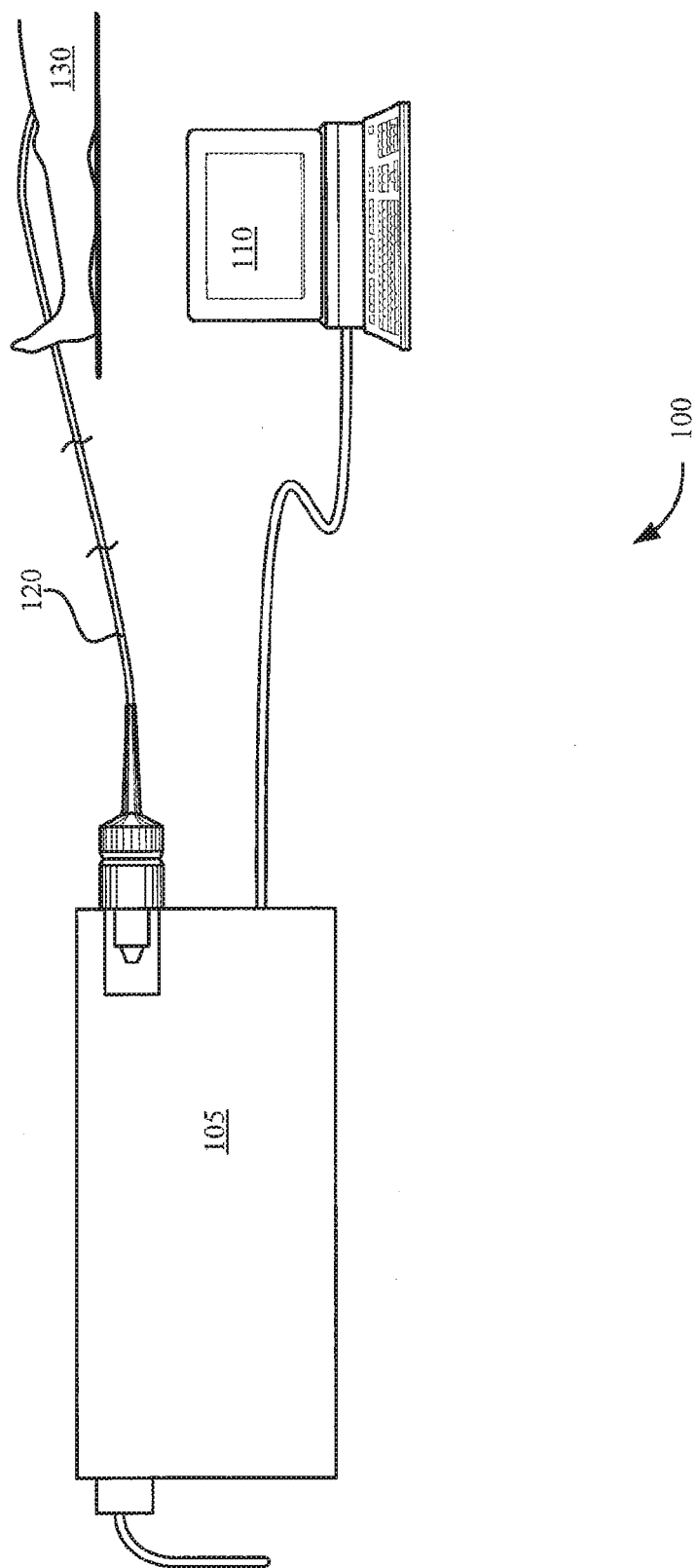
FIG. 1 shows a catheter system according to one embodiment of the invention.

In the appended figures, similar components and/or features may have the same reference label. Where the reference label is used in the specification, the description is applicable to any one of the similar components having the same reference label. Moreover, the figures are not drawn to scale. For example, some components may not be drawn to scale relative to other components.

DETAILED DESCRIPTION

The ensuing description provides various embodiments of the invention only, and is not intended to limit the scope, applicability or configuration of the disclosure. Rather, the ensuing description of the embodiments will provide those skilled in the art with an enabling description for implementing an embodiment. It should be understood that various changes may be made in the function and arrangement of elements without departing from the spirit and scope as set forth in the appended claims.

Embodiments described herein provide for an eccentric balloon catheter. A catheter is provided that includes an elongated catheter body with a cavity (or window) within a peripheral portion of the elongated catheter body near the distal end of the catheter. The cavity exposes a portion of the interior of the catheter body and/or may extend along a portion of the periphery of the catheter body. A balloon may be disposed within the catheter body within the cavity such that when the balloon is deflated or mostly deflated the balloon is contained within the radius of catheter body. When the balloon is inflated the balloon expands and extends through the cavity beyond a portion of the periphery of the catheter body. Moreover, in some embodiments, the balloon may eccentrically located within the catheter body, such that when inflated the balloon inflates generally outwardly in one direction from the axis of the catheter body. In some embodiments, the balloon may be coupled with the catheter body such that the balloon and the elongate housing may move relative to one another.

An eccentric balloon catheter may also include an eccentric guidewire tube that extends at least to the distal end of the catheter and have an aperture at the distal face of the catheter. The eccentric guidewire tube may be positioned eccentric relative to the central axis of the catheter body. Moreover, the guidewire tube may include an inner lumen. The guidewire tube may also extend to the proximal end of the catheter or the guidewire tube may terminate anywhere along the elongated catheter body with a proximal aperture. The guidewire tube, for example, may have an outer diameter of 0.024 inches and an inner diameter of 0.018 inches. The guidewire tube may generally be configured to accept a guidewire and allow the guidewire to slide within the guidewire lumen. The guidewire tube may also be eccentrically arranged within the catheter body. That is, the guidewire tube may not be aligned with the longitudinal central axis of the catheter body, instead, the guidewire tube may be offset between the catheter body central axis and the periphery of the catheter body. In some embodiments, the guidewire tube may be eccentrically located near the same periphery as the cavity. That is, the guidewire tube may extend along a portion of the length of the catheter body parallel to the central axis of the catheter body but off axis with respect to the central axis. In some embodiments, the guidewire tube within the cavity may be exposed to the exterior of the elongate housing. The catheter body may also include one or more light guides, for example, such as a plurality of optical fibers arranged to conduct light from the proximal end of the catheter toward the distal end of the catheter.

Figure 9A:
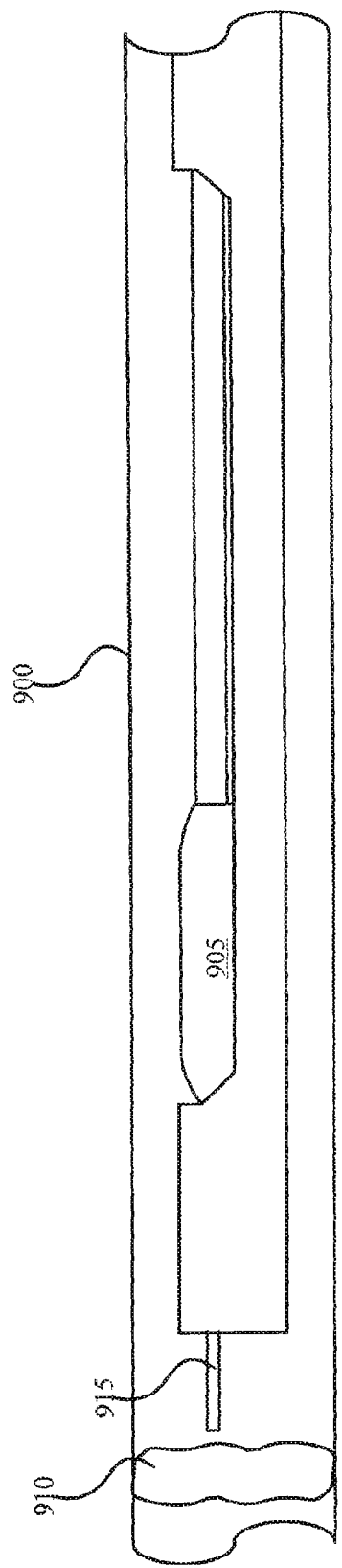
FIGS. 9A, 9B and 9C show an eccentric balloon catheter in various positions within a vessel according to some embodiments.
Figure 9B:
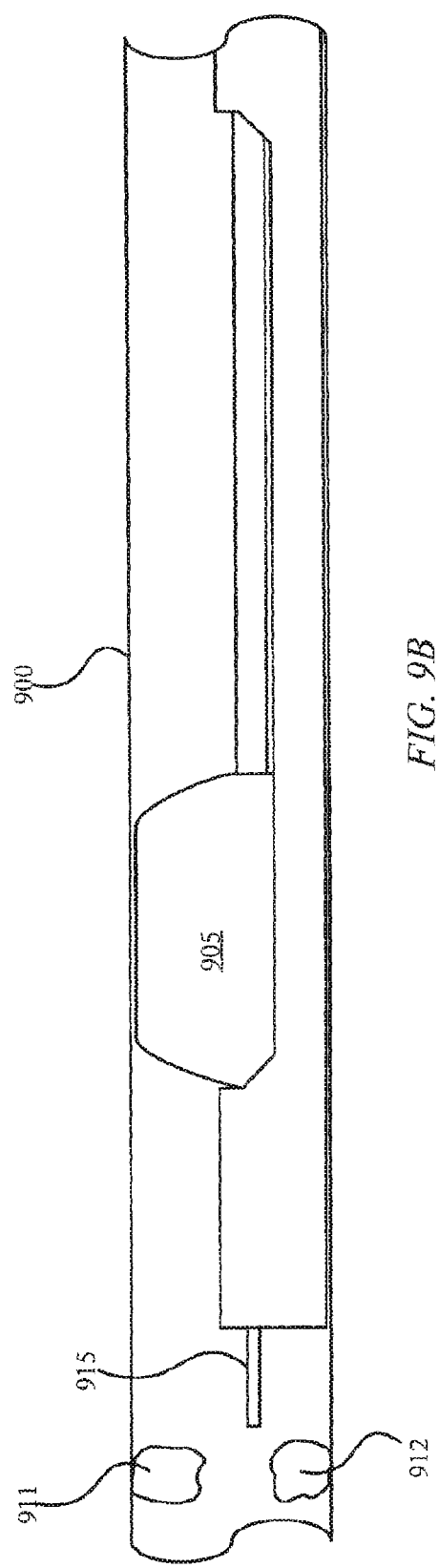

In use, the eccentric balloon catheter may be inserted into a vessel within the human body by following a previously placed guidewire through the guidewire lumen (as shown in FIG. 9A). Once the distal end of the catheter is positioned near a target within the vessel, the catheter may ablate a portion of the target with laser light. The size of the resulting ablation will be at most the diameter of the distal aperture of the fiber optic bundle. In order to ablate a larger cross section within the target, the balloon may be inflated. As the balloon is inflated, the balloon may provide pressure against an inner vessel wall, which may move the catheter laterally within the vessel (as shown in FIG. 9B). After the catheter has moved laterally, the exit aperture of the light guide is now positioned to ablate a previously unablated portion of the target. The balloon may be deflated, the catheter twisted along the central axis, and the balloon inflated to position the exit aperture of the light guide near another unablated portion of the target. If the exit aperture of the light guide is not close enough to the target or too close to the target, the catheter may slide longitudinally relative to the balloon to move into a more ideal position.

FIG. 1 shows a eccentric balloon catheter 100 in use according to one embodiment of the invention. Laser 105 is shown coupled with user interface 110. Laser 105 and user interface 110, in other embodiments of the invention, may be coupled into one system. Laser 105 is connected with catheter 120 that may be inserted into a vessel within a human body 130. Laser 105 and catheter 120 maybe coupled using a laser coupler. Catheter 120 may include an elongated tube that may include a number of elements. Catheter 120 may be of any suitable length A, with a length A between about 50 cm and about 390 cm. For example, the catheter may be 0.04 inches to 0.16 inches in diameter. Catheter 120 may include at least one optical fiber or a bundle of optical fibers that transmits light from laser 105 down at least a portion of the catheter. Some optical fibers may return reflected light back toward laser 105.

The fiber optics within the catheter may receive light from the laser and conduct the light from the proximal end of the catheter to a target from the distal end of the catheter. The catheter may also use liquid or a combination of liquid and optical fibers to conduct light toward the distal end. The light from the laser may be directed toward a target within a vessel using fiber optics within the catheter. The target may be within various biological vessels, for example, blood vessels, arteries, capillaries, organs, etc. In non medical applications, for example, the vessel may include any type a deep cavity within which non-destructive imaging is required, such as, tubes, chambers, pipes, etc.

Figure 2:
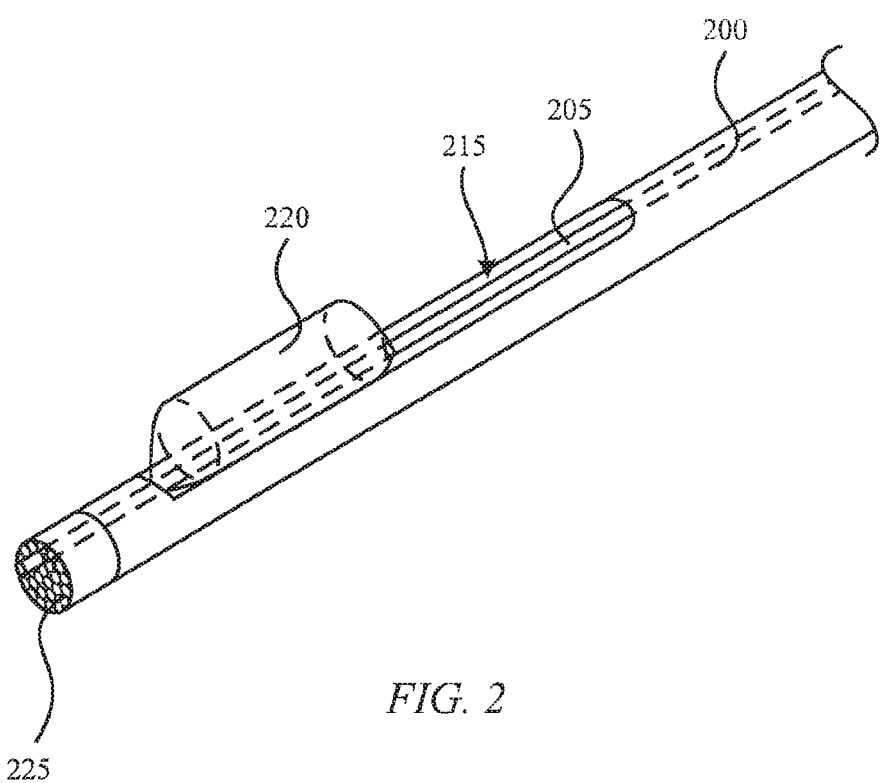
FIG. 2 shows eccentric balloon catheter according to some embodiments.

FIG. 2 shows eccentric balloon catheter including a catheter body 200 with cavity 215 cut through a portion of the periphery of the catheter body. Catheter body 200 may also include distal end 225. Cavity 200 may extend longitudinally for about 1 cm, 5 cm, 10 cm or more along the periphery of the elongated body. Cavity 215 may simply be cut from the periphery of the catheter body and/or may expose portions of the catheter within catheter body 200. Cavity 215 is position on one side of catheter body 200. A guidewire tube 205 may include a guidewire lumen disposed therein and may be disposed within catheter body 200. Guidewire tube 205, for example, may extend to distal end 225 of catheter body 200. At distal end 225, guidewire tube 205 may have an exit port wherein a guidewire may be introduced and slid through the guidewire lumen. Distal end 225 also shows the distal ends of a plurality of fiber optics that extend through the catheter body from the proximal end toward the distal end. The fiber optics may be disposed within the catheter body opposite the guidewire tube. The fiber optics may be replaced with any material that transmits laser light from the proximal end toward the distal end. For example, a liquid light guide may be used singly or in combination with fiber optics.

Balloon 220 is shown inflated and extending from within cavity 215. Balloon 220 may have a diameter of about 2 mm to 4 mm when inflated, according to one embodiment. In some embodiments, balloon 220 may have an inflated diameter up to about 6 mm and as little as 1 mm. In some embodiments, balloon 220 may comprise tubing with a sealed distal end. In some embodiments, the distal end of balloon tubing may have thinner walls and/or a larger diameter such that the distal end inflates under pressure. Balloon 220, for example, may comprise any type of plastic, for example, balloon 220 may comprise nylon, Teflon, urethane, polyethylene, or a mixture thereof. Balloon 220, in some embodiments, may be 10 cm, 9 cm, 8 cm, 7 cm, 6 cm, 5 cm, 4 cm, 3 cm, 2 cm, or 1 cm in length. In some embodiments, balloon 220 may be partially inflated, completely inflated, completely deflated or any level of inflation/deflation in between. Moreover, in some embodiments, balloon 220 may be a compliant balloon which allows for varying inflation diameters without full inflation. In other embodiments, balloon 220 may be non-compliant.

Balloon 220 may also be coupled with a balloon lumen (or balloon tube with an inner lumen) that extends from the proximal portion of the balloon through the catheter body toward the proximal end of the guidewire housing. Balloon lumen may terminate at a balloon port. Balloon lumen may couple with a luer fitting at balloon port. In some embodiments, balloon lumen may bifurcate with the catheter body and be located a distance away from the catheter body. Balloon lumen may include a small diameter lumen. For example, the inner diameter of balloon lumen maybe approximately 0.007 inches. In some embodiments, the inner diameter of balloon lumen may be between 0.005 and 0.015 inches. The outside diameter of balloon lumen, for example, may be 0.016 inches. In some embodiments, the outside diameter of balloon lumen may be 0.05 to 0.007 inches. At the balloon port or luer, balloon lumen may be coupled with a syringe or an indeflator. Balloon 220 may be inflated by injecting fluid through balloon lumen using either a syringe or an indeflator. In some embodiments, the balloon may be inflated using a contrast agent fluid or saline solution. Balloon lumen may include any type of plastic tubing known in the art. For example, balloon lumen may comprise nylon, urethane, Teflon, polyethylene, etc.

Figure 3A:
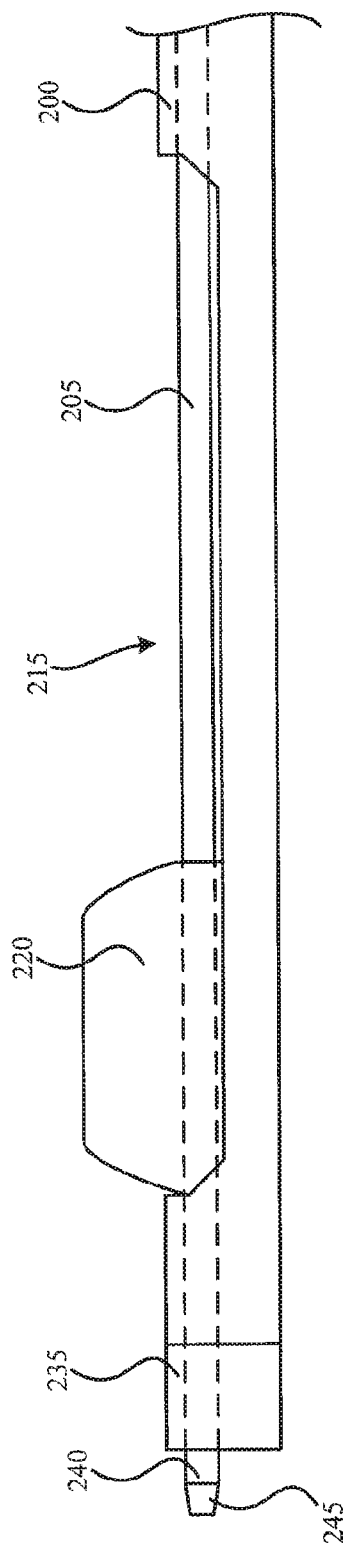
FIGS. 3A and 3B show an eccentric balloon catheter with the balloon inflated and deflated according to some embodiments.
Figure 3B:
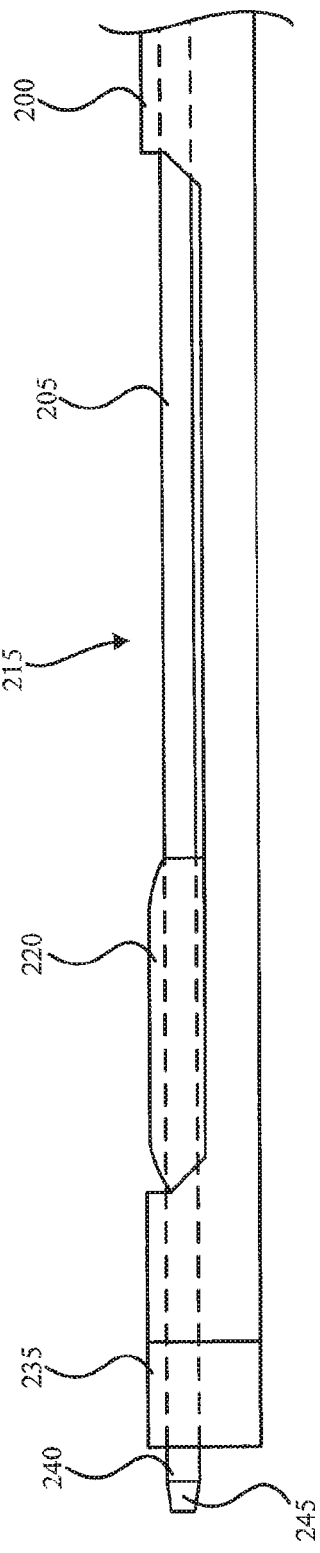

FIG. 3A shows an eccentric balloon catheter with an inflated balloon 220. In some embodiments, when balloon 220 is inflated it extends through cavity 215 (window) past the periphery of the catheter's catheter body 200. FIG. 3B shows an eccentric balloon catheter with a deflated balloon 220. In some embodiments, when balloon 220 is deflated it remains and/or is contained within the periphery of the catheter's catheter body 200 within cavity 215. Balloon 220 may be coupled with a balloon lumen. Balloon 220 inflation tube may then be coupled with an air or liquid pump. The balloon may be inflated by the pump by pumping air or liquid into the balloon. In some embodiments, balloon 220 may be deflated by removing the air or liquid from balloon 220 using the pump. In some embodiments, because balloon 220 is pressurized when inflated, balloon 220 may be deflated by purging the air or liquid from the balloon with or without using the pump. For example, a purge valve may be coupled with the balloon lumen that allows the air or liquid within an inflated balloon to be released when the purge valve is opened.

In some embodiments, balloon 220 may also surround guidewire tube 205. In other embodiments, balloon 220 may be coupled with guidewire tube 205 but does not surround guidewire tube 205.

Figure 4A:
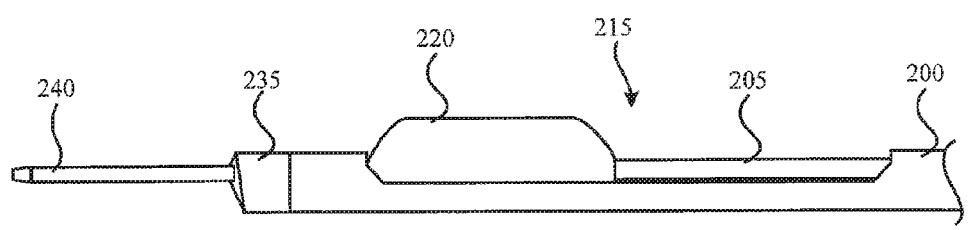
FIGS. 4A and 4B show the slidability of an eccentric balloon catheter according to some embodiments.
Figure 4B:
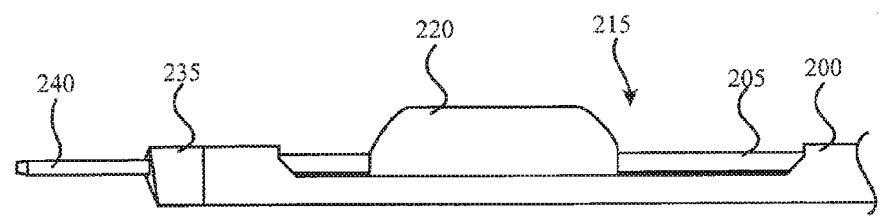

FIGS. 4A and 4B show the slidability of an eccentric balloon catheter according to some embodiments. FIG. 4A shows balloon 220 in a first position near the distal end of cavity 215. FIG. 4B shows balloon 220 in a second position near the middle of cavity 215. As shown, balloon 220 may slide relative to catheter body 200. Moreover, catheter body 200, including a light guide disposed therein and or guidewire tube 205, may move relative to balloon 220. Hence, catheter body 200 with the light guide may be advanced over a guidewire toward a target while balloon 220 is inflated and held relatively in position.

Figure 8:
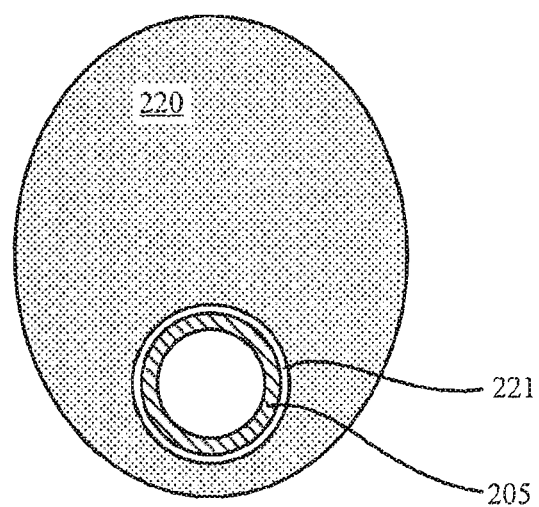
FIG. 8 shows a cut away of an eccentric balloon surrounding a guidewire tube according to one embodiment.

In some embodiments, balloon 220 is coupled with a rail and/or track system that enables balloon 220 and catheter body 200 to slide relative to one another. For example, as shown in FIG. 8, guidewire tube 205 may include a stiff and/or slick exterior surface that, at least within cavity 215. Balloon 220 may include an inner lumen 221 that slides over guidewire tube 205. In some embodiments, guidewire tube 205 may have a slick or lubricated surface to allow balloon lumen 221 to slide relative to guidewire tube 205. In some embodiments, balloon 220 and catheter body 200 may be coupled with a plunger, such as a spring loaded plunger, at the proximal end of the eccentric balloon catheter, which may be used to actuate balloon 220 relative to catheter body 200.

Figure 5A:
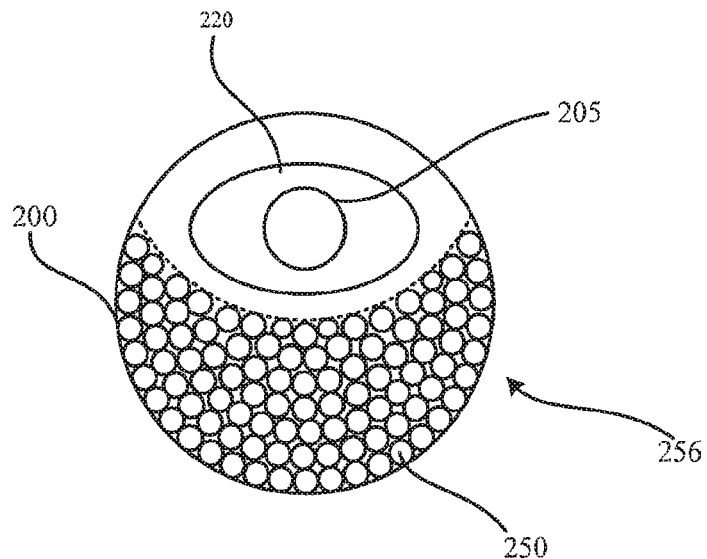
FIGS. 5A and 5B show a distal end view of an inflated and deflated eccentric balloon catheter according to some embodiments.
Figure 5B:
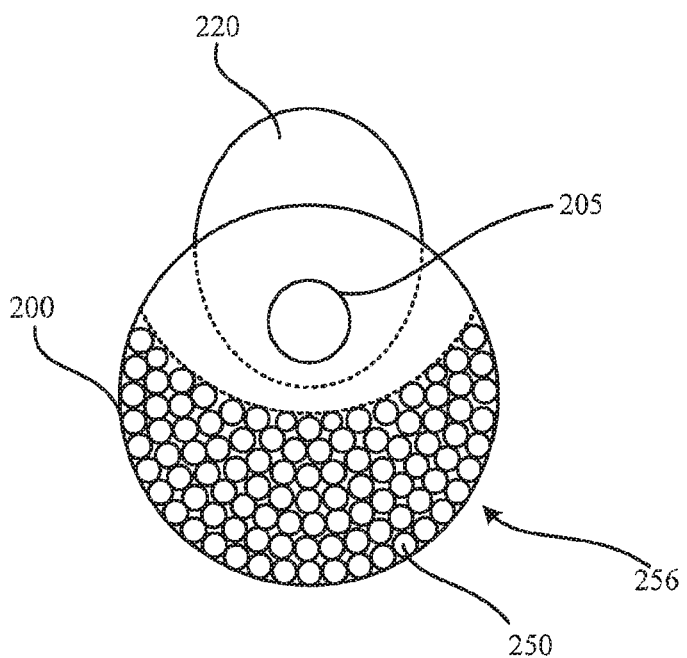

FIG. 5A show a distal end view of deflated eccentric balloon catheter according to some embodiments. As shown in some embodiments, balloon 220 is contained within the periphery of catheter body 200 when deflated. Also, in some embodiments, balloon 220 is surrounds guidewire tube 205. FIG. 5B shows a distal end view of inflated eccentric balloon catheter. As shown in some embodiments, balloon 220 extends outside the periphery of catheter body 200 when inflated. Both figures also show the distal ends of a plurality of fiber optics 250 arranged in a bundle. Fiber optics 250, in some embodiments, may be contained within light guide lumen 256 that separates them from cavity 215 and/or guidewire tube 205. In some embodiments, fiber optics 250 may not be contained within a lumen and, therefore, a portion of fiber optics 250 may be exposed by cavity 215.

Figure 6:
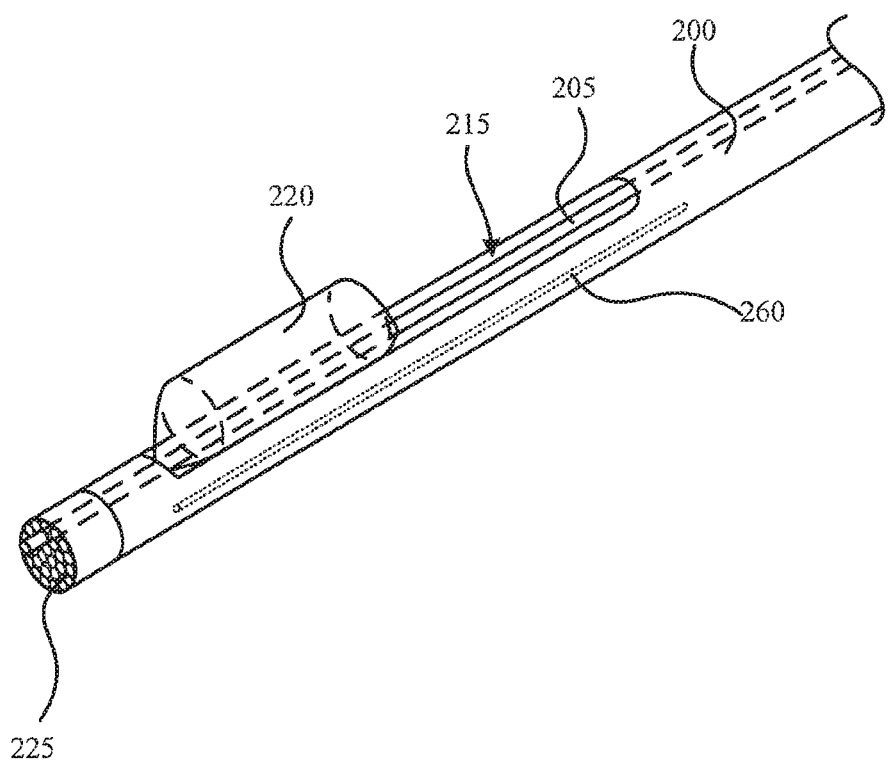
FIG. 6 shows an eccentric balloon catheter with a straightening stylet included within the catheter according to some embodiments.

FIG. 6 shows an eccentric balloon catheter with a straightening stylet (or rib) 260 included within the catheter according to some embodiments. Straightening stylet 260 may provide added support to the portion of catheter body 200 near cavity 205. Moreover, straightening stylet 260 may provide structural strength, stiffness, and/or keep the distal end of catheter body 205 and the catheter from bending. Straightening stylet 260 may also ensure proper biasing of the distal end of the catheter when balloon 220 is inflated. In some embodiments, straightening stylet 260 may be coupled with catheter body 200. In some embodiments, straightening stylet 260 may be inserted within the catheter during use. In some embodiments, straightening stylet 260 may be inserted within catheter body 200 after inflation of balloon 220.

Figure 7:
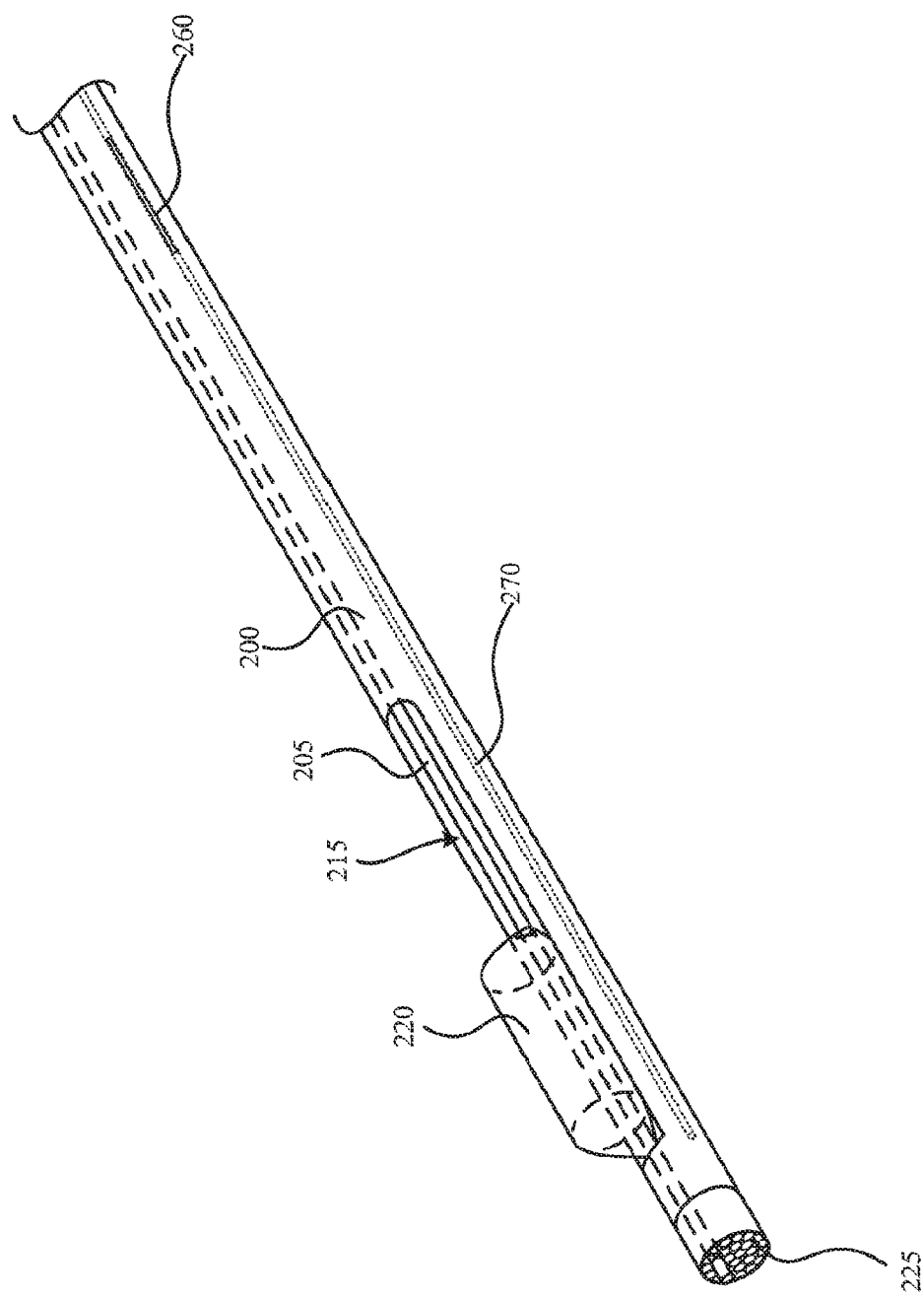
FIG. 7 shows an eccentric balloon catheter with a stylet lumen according to some embodiments.

In some embodiments, eccentric balloon catheter may include stylet lumen 270 disposed, for example, within catheter body 200 and/or within the light guide, as shown in FIG. 7. For example, stylet lumen 270 may be disposed within a fiber optic bundle. Straightening stylet 260 may be located within the proximal end of the stylet lumen 270 prior to use. In use, straightening stylet 260 may be moved toward the distal end of the eccentric balloon catheter; for example, near cavity 215 to provide stiffness to the portion of catheter body 200 near cavity 215. Stylet lumen 270 and/or straightening stylet 260 may be coupled with a plunger to move straightening stylet 260 toward the distal end of the catheter.

Figure 9C:
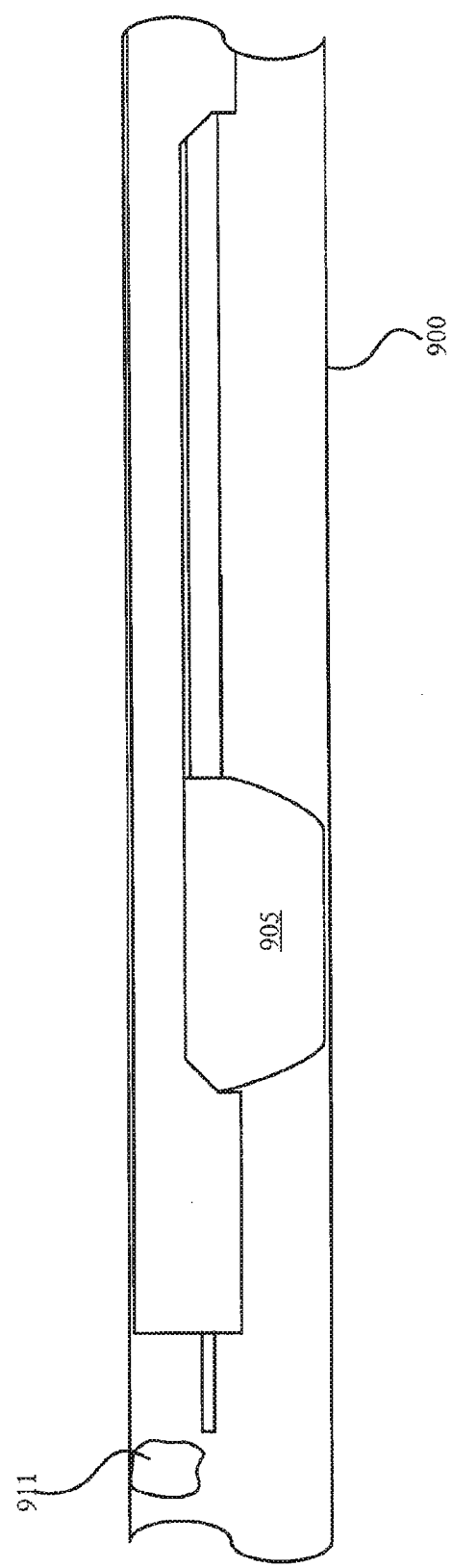

FIG. 9A shows an eccentric balloon laser catheter positioned near target 910 within a vessel 900 with balloon 905 deflated. Eccentric balloon laser catheter may be positioned using guidewire 915. In position, eccentric laser catheter may ablate at least a portion of target 910. FIG. 9B shows target 910 ablated through the middle leaving two portions of target 911, 912. Moreover, FIG. 9B shows eccentric balloon 905 inflated and pressed against a wall of vessel 900 shifting eccentric balloon laser catheter within vessel 900. In this position, eccentric balloon laser catheter may ablate target portion 912. Balloon 905 may be deflated, eccentric balloon laser catheter may be rotated, for example, about 180°, and balloon 905 inflated, as shown in FIG. 9C. In this position, target portion 911 may be ablated. In some embodiments, the catheter or the light guide may be advanced relative to balloon 905.

Figure 10:
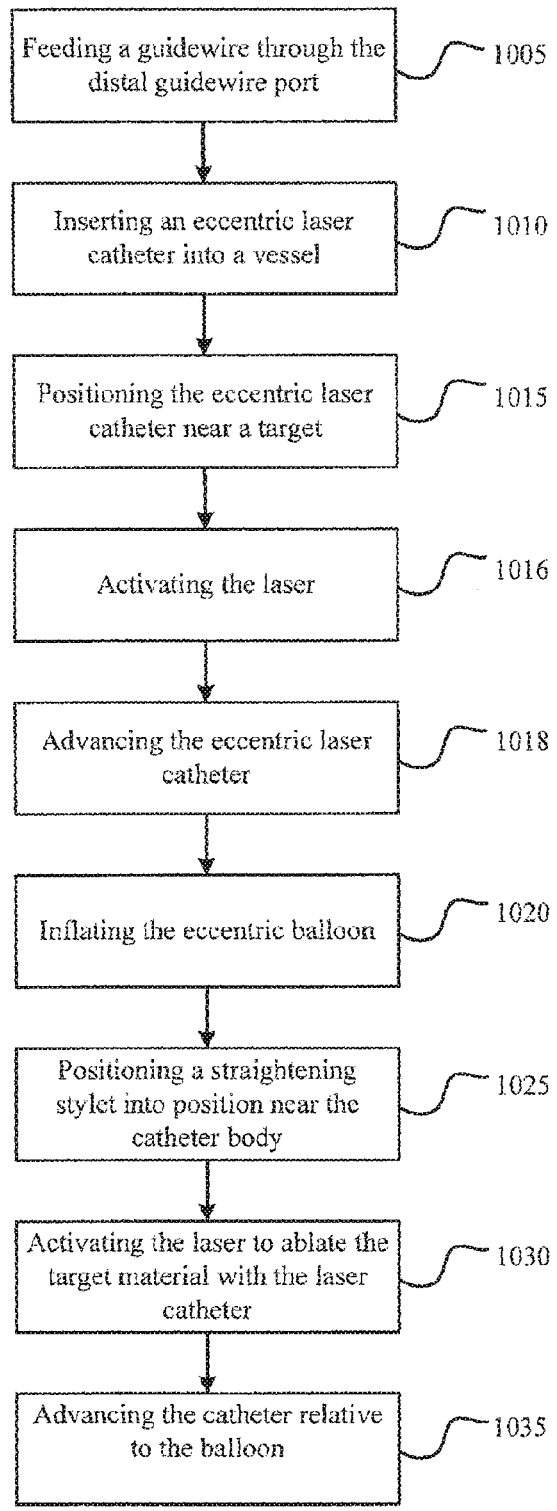
FIG. 10 shows a flowchart depicting a method for using a balloon catheter according to some embodiments.
Figure 11:
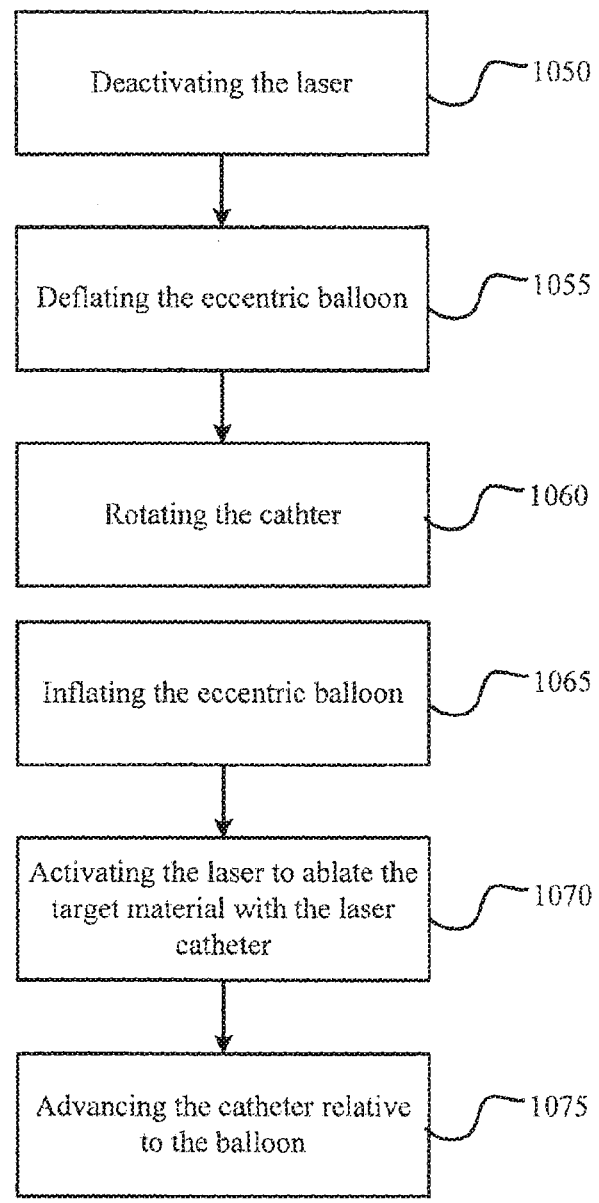
FIG. 11 shows another flowchart depicting a method for using a balloon catheter according to some embodiments.

FIG. 10 shows a flowchart of a method of using an eccentric balloon catheter according to one embodiment. Some steps may be omitted and others added to what is shown in FIG. 10 and/or what is described herein. The proximal end of a guidewire is fed, for example, through a guidewire lumen starting at the guidewire port at block 1005. The guidewire may have been previously positioned within the vessel. The catheter may then be inserted into the vessel by feeding the catheter over the guidewire tube until the catheter is positioned at or near a target at blocks 1010 and 1015. Once at the target, the laser may be activated at block 1016, and the eccentric balloon catheter may be advanced through the lesion ablating a portion of the target at block 1018, creating a pilot channel. Once the pilot channel has been ablated the laser catheter may be deactivated and/or repositioned. In order to ablate the periphery of the target and/or the pilot channel, for example, the eccentric balloon may be inflated causing the catheter to axially shift within the vessel at block 1020. Because of this axial shift, the distal end of the catheter may not be in position to ablate material near the vessel walls. Accordingly, at block 1025, a stiffening stylet may be inserted into the catheter to provide lateral support near where the balloon is exerting pressure. The stiffening stylet may be inserted at any time during the procedure. The laser may then be activated ablating target material at block 1030 and the catheter may optionally be advanced while the balloon is held relatively in place at block 1035.

What is claimed is:

1. A method for using a catheter, the method comprising:
   (a) inserting the catheter into a vessel, wherein the catheter comprises (i) a catheter body including a central axis, a proximal end, a distal end face, and a cavity disposed within a periphery of the catheter body, (ii) a light guide extending from the proximal end of the catheter body to the distal end face of the catheter body, and (iii) a balloon coupled with the catheter body, wherein at least a first portion of the balloon is disposed within the cavity;
   (b) coupling a laser to the light guide;
   (c) positioning the catheter near a target within the vessel;
   (d) activating the laser while the balloon is in an uninflated state and ablating at least a first portion of the target;
   (e) inflating the balloon to an inflated state, after activating the laser while the balloon is in the uninflated state, thereby causing at least a second portion of the inflated balloon to extend outside the cavity eccentrically relative to the catheter body and proximally relative to the distal end face of the catheter body and press against an inner wall of the vessel or the target;
   (f) activating the laser while the balloon is in the inflated state and ablating at least a second portion of the target; and
   (g) axially moving the distal end face of the catheter body relative to the balloon in a longitudinal direction of the central axis within the vessel while the balloon is in the inflated state.

2. The method according to claim 1, wherein (d) activating the laser while the balloon is in the uninflated state and ablating at least the first portion of the target comprises forming a pilot channel in the target.

3. The method according to claim 1, further comprising deflating the balloon to the deflated state after (g) axially moving the distal end face of the catheter body relative to the balloon in a longitudinal direction of the central axis within the vessel while the balloon is in the inflated state.

4. The method according to claim 3, further comprising axially rotating the catheter after deflating the balloon to the deflated state.

5. The method according to claim 4, further comprising inflating the balloon to the inflated state after axially rotating the catheter.

6. The method according to claim 5, further comprising activating the laser while the balloon is in the inflated state after axially rotating the catheter and ablating at least a third portion of the target.

7. The method according to claim 1, further comprising inserting a straightening stylet into the catheter body after (e) inflating the balloon to the inflated state.

8. The method according to claim 1, further comprising inserting a guidewire within a guidewire tube within the catheter.

9. A method for using a catheter, the method comprising:
(a) inserting the catheter into a vessel, wherein the catheter comprises (i) a catheter body including a central axis, a proximal end, a distal end face, and a cavity disposed within a periphery of the catheter body, (ii) a light guide disposed within the catheter body, and (iii) a balloon, wherein at least a first portion of the balloon is disposed within the cavity;
(b) positioning the catheter adjacent a target within the vessel;
(c) activating a laser coupled to the light guide while the balloon is in an uninflated state and ablating at least a first portion of the target;
(d) inflating the balloon to an inflated state, thereby causing at least a second portion of the inflated balloon to extend outside the cavity eccentrically relative to the catheter body and proximally relative to the distal end face of the catheter;
(e) activating the laser while the balloon is in the inflated state and ablating at least a second portion of the target; and
(f) advancing the catheter body relative to the balloon while the balloon is in the inflated state.

10. The method according to claim 1, wherein (c) activating the laser while the balloon is in the uninflated state and ablating at least the first portion of the target comprises forming a pilot channel in the target.

11. The method according to claim 1, further comprising axially moving the distal end face of the catheter body relative to the balloon in a longitudinal direction of the central axis within the vessel while the balloon is in the inflated state.

12. The method according to claim 1, further comprising deflating the balloon to the deflated state after (f) advancing the catheter body relative to the balloon while the balloon is in the inflated state.

13. The method according to claim 12, further comprising axially rotating the catheter after deflating the balloon to the deflated state.

14. The method according to claim 13, further comprising inflating the balloon to the inflated state after axially rotating the catheter.

15. The method according to claim 14, further comprising activating the laser while the balloon is in the inflated state after axially rotating the catheter and ablating at least a third portion of the target.

16. The method according to claim 9, further comprising inserting a straightening stylet into the catheter body after (d) inflating the balloon to the inflated state.

17. The method according to claim 9, further comprising inserting a guidewire within a guidewire tube within the catheter.

18. A method for using a catheter, the method comprising:
inserting the catheter into a vessel, wherein the catheter comprises:
a catheter body including a light guide disposed therein, the catheter body having a central axis, a proximal end, a distal end face, and a cavity disposed within a periphery of the catheter body, and,
a balloon slidably coupled with the catheter body, wherein at least a first portion of the balloon is disposed within the cavity;
positioning the catheter adjacent a target within the vessel;
activating a laser while the balloon is in an uninflated state and ablating at least a first portion of the target;
inflating the balloon to an inflated state, thereby causing the inflated balloon to extend outside the cavity eccentrically relative to the catheter body and proximally relative to the distal end face of the catheter body;
activating the laser while the balloon is in the inflated state and ablating at least a second portion of the target; and,
slidably repositioning the catheter adjacent the target while the balloon remains stationary.

19. The method according to claim 18, wherein slidably repositioning the catheter further comprises advancing the catheter body relative to the balloon while the balloon is in the inflated state.

20. The method according to claim 18, wherein slidably repositioning the catheter further comprises axially moving the distal end face of the catheter body relative to the balloon in a longitudinal direction of the central axis within the vessel while the balloon is in the inflated state.

* * * * *